United States Patent [19]

Simmons et al.

[11] Patent Number: 5,527,530
[45] Date of Patent: Jun. 18, 1996

[54] ALCOHOLIC MOISTURIZING AFTER SHAVE LOTION

[75] Inventors: Mason S. Simmons, West Chester; Louis S. Lisboa, Cincinnati; Elizabeth A. Ferguson, Fairfield, all of Ohio

[73] Assignee: The Procter & Gamble Company, Cincinnati, Ohio

[21] Appl. No.: 272,170

[22] Filed: Jul. 8, 1994

[51] Int. Cl.⁶ ..................... A61K 7/15
[52] U.S. Cl. ............ 424/401; 424/73; 424/78.03; 424/78.05; 424/78.06; 514/847; 514/848; 514/887
[58] Field of Search ............... 424/401, 73, 70, 424/78.03, 78.05, 78.06; 514/847, 848, 887

[56] References Cited

U.S. PATENT DOCUMENTS

| | | | |
|---|---|---|---|
| 3,728,447 | 4/1973 | Osipow et al. | 424/70 |
| 4,136,163 | 1/1979 | Watson et al. | 424/73 |
| 4,230,688 | 10/1980 | Rowsell et al. | 424/73 |
| 4,272,544 | 6/1981 | Cella et al. | 424/401 |
| 4,279,891 | 7/1981 | Henkel et al. | 424/59 |
| 4,690,784 | 9/1987 | Nanba et al. | 260/403 |
| 4,758,376 | 7/1988 | Hirota et al. | 424/70 |
| 4,758,599 | 7/1988 | Minetti | 514/844 |
| 4,761,278 | 8/1988 | Lewis et al. | 424/73 |
| 5,039,513 | 8/1991 | Chatterjee et al. | 424/47 |
| 5,139,784 | 8/1992 | Ciaudelli | 424/401 |

FOREIGN PATENT DOCUMENTS

WO93-25177 12/1993 WIPO.

OTHER PUBLICATIONS

Proserpio, Gianni, *Chemical Abstracts*, vol. 101(18), Oct. 29, 1984, #157457.

Kanebo, *Chemical Abstracts*, vol. 98(10), Mar. 7, 1983, #77947v.

Nomura, *Chemical Abstracts*, vol. 120(2), Jan. 10, 1994, #14640s.

Buenning, Einhard, *Chemical Abstracts*, vol. 118(12), Mar. 22, 1993, #109381F.

Baiocchi, F; Jennings, D; and DelVecchio, A. J., "Use of acyl lactylates in cosmetics and toiletries", *Cosmetics and Perfumery* for Sep., 1975.

Baiocchi, F. & France, J. R., Technology Report, "Sodium isostearoyl-2-lactylate in cosmetics and toiletries" *Cosmetics and Toiletries*, vol. 93, No. 1, p. 47.

Pationic™ ISL Moisture Retention Study Technical Data Sheet, 183–1, RITA Corporation.

CTFA Cosmetic Ingredient Handbook, The Cosmetic, Toiletry and Fragrance Association, Inc., pp. 272–273, 1992.

Berger, Frank J and Megerle, George H., "Hair Conditioners, Lacquers, Setting Lotions and Rinses", *Cosmetics Science and Technology*, 1972, Wiley-Interscience; Ed. Balsam & Sagarin, pp. 349–351.

Weiser, H. et al., "Accelerating of Superficial Wound Healing by Panthenol Zn Oxide", *Cosmetic & Toiletries*, vol. 103, pp. 79–84, Oct. 1988.

*Primary Examiner*—Thurman K. Page
*Attorney, Agent, or Firm*—John M. Howell; Carl J. Roof; David K. Dabbiere

[57] ABSTRACT

The present invention is for an alcoholic moisturizing after shave lotion having reduced stinging and burning upon application. Said lotion contains a combination of an anti-inflamatory agent and a moisturizing emollient within specified ratios to one another for elimination of stinging and burning when applying said lotion to the skin.

14 Claims, No Drawings

ALCOHOLIC MOISTURIZING AFTER SHAVE LOTION

TECHNICAL FIELD

The present invention is for an alcoholic moisturizing after shave lotion having reduced stinging and burning upon application, particularly to skin having recently been shaven.

BACKGROUND OF THE INVENTION

After shave lotions applied to the skin, particularly those containing fragrances are well known in the art. Typically after shave lotions are alcohol/water based systems used for fragrance presentation and while they may be applied at any time, are frequently applied after shaving; thus, the nomenclature. For the present discussion, after shave lotion means alcoholic lotions applied to the skin at any time in order to obtain desirable cosmetic characteristics.

After shave lotions typically contain significant levels of alcohol, typically from about 50% to about 90% ethanol, as described in U.S. Pat. No. 4,761,278, Lewis et al., issued Aug. 2, 1988 and U.S. Pat. No. 4,758,599, Minetti, issued Jul. 19, 1988; both herein incorporated herein by reference. While such lotions provide a cooling effect and skin tightening feeling, they also cause stinging and burning of skin, particularly skin having been shaved with a razor blade. Furthermore, such lotions have little or no skin moisturization properties.

Alternatively, the level of alcohol in skin lotions have been reduced to mitigate stinging and burning. U.S. Pat No. 4,279,891, Henkel et al., issued Jul. 21, 1981 discloses clear after shave lotions containing from about 15% to about 20% ethanol and additional components such as water, perfume, propylene glycol and ethoxylated alcohol and betaine surfactant perfume solubilizer. Solubilization of perfumes in low ethanol ethanol/water based systems is disclosed in *The HLB System*, ICI Americas Incorporated, May 1992; incorporated herein by reference. These lotions, however, do not provide the user with positive skin feel attributes due to ingredients such emulsifiers added in order to keep the perfume from separating from the low ethanol/water system.

Alcoholic after shave lotions containing ingredients to off-set the negative effects of high levels of alcohol are known in the art. U.S. Pat. No. 4,758,599, Minetti, issued Jul. 19, 1988 discloses hydro-alcoholic after shave lotions providing moisturization and protection from infection while mitigating skin irritation. Said compositions disclosed therein combine from about 50% to 90% lower alcohols; niacinamide, a commonly known vasodilator; sodium lactate, a moisturizer; quarernuim 26, an emollient; and water.

Moisturizers are commonly used in cosmetic compositions for skin care benefits. Such moisturizers are disclosed in U.S. Pat. No. 5,139,784, Claudelli, issued Aug. 18, 1992, and U.S. Pat. No. 4,690,774, Nanba et al., issued Sep. 1, 1987; both incorporated herein by reference. These patents disclose emulsions or thickened liquids lotions for topical application that provide humectancy or moisturization to the skin. Consumers using such moisturizing lotions, however, experience cosmetic negatives during application, such as tackiness, and after dry down, such as residue left on the skin.

Anti-inflamatory agents are known for use in lotions for reduction of skin irritation. It has been reported that panthenol in combination with zinc oxide provides an acceleration of superficial wound healing (see H. Weise et al., *Acceleration of Superficial Wound Healing by Panthenol Zinc Oxide*, Cosmetics and Toiletries, Vol. 103, pp. 79–84, October 1988). Combinations of panthenol and salicylic acid are also known for use in skin care compositions, particularly anti-acne products as disclosed in U.S. Pat. No. 5,015,470, Gibson, issued May 14, 1991 discloses topical lotions for skin or hair growth containing salicylic acid and panthenol. Panthenol alone is known for use in a number of cosmetic compositions including after shave lotions to reduce skin irritation.

It is believed that skin irritation reported in said references differs than the immediate sting and burn caused by application of an alcoholic lotions to the face. The application of alcoholic based products to the skin, particularly freshly shaven skin, produces immediate sting and burn, often referred to as a "bite". Despite the teachings in these references, panthenol is not known to eliminate or significantly mitigate bite.

Moisturizing emollients are known in the art for use in cosmetic compositions. One group of such moisturizing emollients known in the art are acyl lactylates; see F. Baiocchi et al., *Use of Acyl Lactylates in Cosmetics and Toiletries*, Cosmetics and Perfumery, September 1975. Acyl lactylate are anionic surface-active agents prepared from naturally occurring raw materials, fatty acids, and lactic acid normally found in skin tissue. They are typical used in cosmetics as emulsifiers, opacifiers, viscosity builders, skin feel modifiers, and moisturizing agents, however, are not known to have a singificant effect on stinging and burning of skin when applied in an alcoholic lotion.

The present invention is for alcoholic after shave lotion which effectively mitigate or eliminate stinging or burning and provide effective moisturization of the skin without compromising good cosmetic feel on the skin. The combination of moisturizing emollient and anti-inflammatory agent in alcoholic lotions provides unexpected relief from burning and stinging of the skin.

SUMMARY OF THE INVENTION

The present invention is a clear lotion for use on the skin wherein said lotion provides a cooling effect without subjecting the user to stinging and burning normally associated with hydroalcoholic solutions. Another object of the present invention is to provide an after shave lotion which imparts the above-mentioned attributes. It is a further object of the present invention to provide an after shave lotion which contains additional ingredients which provide conditioning benefits to the skin.

The present invention comprises:

a. from about 20% to about 80% of a $C_1$ to $C_6$ monohydric alcohol;

b. from about 0.5% to about 5.0% of an anti-inflammatory agent; selected from derivatives of pantothenic acid, pantothenic ether, and mixtures thereof; and c. from about 0.5% to about 5.0% of a moisturizing emollient wherein the moisturizing emollient is an acyl lactylate having the formula:

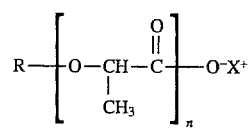

wherein R is a branched, straight, or combinations of a $C_6$ to $C_{30}$ branched and straight chained alkoyl groups; X is an alkali metal, and n is from about 1 to about 4; wherein the ratio of moisturizing emollient to anti-inflammatory agent is from about 1:5 to about 5:1.

The combination of the anti-inflammatory agent and moisturizing emollient in the ratios disclosed above provides suprisingly greater relief from burning and stinging as compared to the effects on stinging and burning achieved by each ingredient individually. The compositions of the present invention may also include other cosmetic ingredients to impart desirable skin feel properties as well as further skin conditioning benefits.

DETAILED DESCRIPTION OF THE INVENTION

A. Alcohols

Alcohols are used in the present invention at levels from about 20% to about 80%, preferably from about 50% to about 70%, and most preferably from about 55% to about 65% of the composition. The alcohols used in the present invention are $C_1$ to $C_6$ monohydric alcohols; preferably those seleected from the group consisting of include methanol, ethanol, isopropanol, propanol and mixtures thereof; most preferably ethanol. These alcohols provide cooling due their volatility and heat of vaporization, clean cosmetics due to their complete volatilization from the skin surface, solubilization of hydrophobic ingredients such as perfumes, and antisepsis.

B. Anti-Inflammatory Agent

The present invention comprises from about 0.5% to about 5.0%, preferably from about 1.0% to about 4.0%, and most preferably from about 1.5% to about 3.0% of an anti-inflammatory agent. Said anti-inflammatory agent is selected from the group consisting of derivatives of pantothenic acid, pantothenic ether, and mixtures thereof. The anti-inflammatory agent is preferably an alcohol derivative of pantothenic acid, disclosed as panthenol in *CTFA Cosmetic Ingredient Handbook*, The Cosmetic, Toiletry and Fragrance Association. Inc. pp.272–273, 1992. Included are panthenol's enantiomers or d-panthenol and/panthenol, preferably d-panthenol. The preferable form is panthenol since it is soluble in both alcohols and polar solvents and it is commercial availability.

C. Moisturizing Emollient

The present invention contains from about 0.5% to about 5.0%, preferably from about 1.0% to about 4.0%, most preferably from about 1.5% to about 3.0% of a mositurizing emollient comprising an acyl lactylate having the following formula

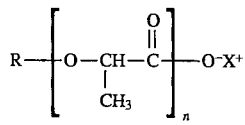

wherein R are branched, straight, and a combination of a branched and astraight chained alkoyl group having from about 6 to about 30 carbons, preferably selected from the group consisting of caproyl, myristoyl, stearoyl, lauroyl, and mixtures thereof; X is an alkali metal, preferably selected from the group consisting of sodium, potassium and mixtures thereof; and n is from about 1 to about 4, wherein the ratio of said moisturizing emollient to anti-inflammatory agent is from about 1:5 to about 5:1, preferably from about 2:7 to about 7:2 and most preferably from about 2:1 to about 1:2.

Said acyl lactylates are combinations of fatty acids and lactic acid synthesized in the presence of an alkali metal or an alkaline earth ion. The general reaction can be found in Baiocchi, Jennings, and Del Vecchio, *Use of Acyl Lactylates In Cosmetics and Toiletries*, Cosmetics and Perfumery, September 1975, incorporated herein by reference.

The preferred acyl lactylate has an R group comprising a branched $C_{17}H_{35}CO$ isostearoyl group, n being from about 1 to about 3, and X being sodium. The acyl lactylate most preferred is sodium isostrearoyl-2-latcylate available from C. J. Patterson Company, Kansas City Mo. as Pationic, ISL. It is reported in the technical data available from C. J. Patterson, incorporated herein by reference, that sodium isostearoyl-2-latcylate is able to retain a significantly greater percentage of absorbed moisture as the relative humidity is decreased than either propylene glycol or glycerin.

D. Optional Ingredients

The present invention may include a number of optional ingredients at levels necessary to achieve desirable compositional aesthetics, fragrance presentation, or skin feel and conditioning benefits to the skin. The following is a non-limiting disclosure of typical optional ingredients to be used together with the claimed invention.

Polar Co-Solvents

Polar co-solvents may be used with the alcohol solvent in the present invention. Said co-solvents include propylene glycol, dipropylene glycol, water, and mixtures thereof. Water is a particularly useful co-solvent since it is inexpensive and has little or no skin irritation properties. Water may be used in amounts necessary to provide good aesthetics, but, limited to levels that do not directly or indirectly create objectionable skin feel characteristics. Typical water levels in compositions of the present invention are from about 10% to about 80%, preferably from about 30% to about 50%.

Skin Conditioning Agents

Skin conditioning agents are also useful in the present invention to provide the user with desirable characteristics such as good glide over the skin upon application, dry feeling, smooth skin after dry down, and soft skin. Typical skin conditioning agents as found *CTFA Cosmetic Ingredient Handbook*, The Cosmetic, Toiletry and Fragrance Association. Inc. pp.572–580, incorporated herein by reference. Said conditioning agents include, but, are not necessarily limited to silks, powders, silicones and other known ingredients providing the above mentioned attributes. For example, a solution of fibroin silk leaves a smooth, desirable skin feel after dry down. Additionally, dimethicone copolyols also provide desirable skin feel. Said skin conditioning agents are used at levels necessary to provide the desired skin feel characteristic sought by the formulator, however, typically the levels used in the present invention are from about 0.05% to about 6.0%, preferably from about 0.20% to about 2.0%, more preferably from about 0.20% to about 0.75%, and most preferably from about 0.30% to about 0.50% of the composition.

Skin Coolants

Skin coolants are useful herein and include but, are not limited to those disclosed in U.S. Pat. No. 4,230,688, Rowsell,et al., issued Oct. 28, 1990 (Wilkinson Sword Limited, England) which is incorporated herein by reference; and 3-substituted-p-methanes as described in U.S. Pat. No. 4,136,163 Watson et al., issued Jan. 23, 1979 (Wilkinson Sword Limited, England) which is incorporated herein by reference. Specific coolants used in the present invention are N,2, 3,-trimethyl-2-isopropylbutanamide, N-ethyl p-methan-3-carboxamide,and mixtures thereof, at levels from about 0.05% to about 1.0%, preferably from about 0.01% to about 0.25% of the composition, wherein the mixture is a ratio of N,2, 3,-trimethyl-2-isopropylbutanamide to N-ethyl p-methan-3-carboxamide from about 1:5 to about 3:1 as disclosed in PCT Application WO 93-05455 published Dec. 23, 1993; incorporated herein by reference.

Fragrance

The compositions hereof will generally contain a fragrance or perfume to impart a desired aroma, or to mask odors that may be associated with other components of the compositions. Any perfume suitable for application to the skin can be used. A wide variety of perfumes and perfumes are known to those skilled in the art and are commercially available. The particular perfume used is largely a matter of choice, however, the perfume should be used at a level effective for providing a noticeable aroma to the composition, or for masking undesired aroma of the composition. In general, the compositions will comprise from about 0.1% to about 10% of a fragrance component. For the present invention, the fragrance level is preferably from about 0.1% to about 5.0%; more preferably from about 2.0% to about 4.0%. Fragrances as used in the present invention are defined as volatile, odoriferous, component of one or more active fragrance compounds which exude pleasant or otherwise desired aromas at ambient conditions. The fragrance comprises odoriferous fragrance active compounds and may also include additional ingredients, such as diluents, solvents for solid fragrance ingredients, and fixatives, etc.

The fragrances hereof are, in general, liquids at ambient temperature and are characterized by a flash point of from about 10° C. to about 120° C., more typically from about 25° C. to about 95° C. (as determined according to ASTM D-56 (c.c.)—Standard Test Method for Flash Point by Tag Closed Tester).

The fragrance active compounds are typically incorporated into the fragrance components in liquid form, but can also be solids (such as the various camphoraceous fragrances known in the art) which are solubilized in other ingredients of the fragrance component.

As discussed, in addition to the fragrance active compounds, the fragrance hereof can also include additional ingredients such as diluents, solvents for solid fragrance ingredients, and fixatives, etc. Diluents may or may not have their own aroma and, to the extent that they do, they are categorized as fragrance active compounds. Exemplary diluents and solvents include alcohols (e.g. ethyl alcohol, benzyl alcohol, dipropylene glycol, etc.) and liquid hydrocarbon and hydrocarbon esters (e.g., benzyl benzoate and other hydrocarbons and esters described above). Fixatives are ingredients which prolong the lasting quality of the fragrance upon use and can do so by modifying the overall volatility of the fragrance component. Some fixatives can function as fragrance active compounds, whereas others do not. To the extent that a particular ingredient performs both functions, it shall be considered a fragrance active compound. Exemplary fixatives include musk fragrance ingredients described below.

A wide variety of fragrance active compounds are described in S. Arctander, Perfume, Flavors and Chemicals, Vols, I and II, Author, Montclair, N.J., the Merck Index, 8th Edition, Merck & Co., Inc., Rahway, N.J., and Secondini, Handbook of Perfumes and Flavors, Chemical Publishing Co., Inc., New York, N.Y., 1990 (ISBN) 0-8206-0334-1), incorporated herein by reference.

The typical fragrance will comprise a plurality of individual fragrance active compounds, although it can consist essentially of a single fragrance ingredient. It is well within the scope of the fragrancer of ordinary skill in the art changing ingredients in the fragrance component and/or modifying the relative levels of fragrance ingredients.

Various types of chemical compounds are commonly known for use as a fragrance including: phenolic compounds; essential oils; aldehydes; ketones; polycyclic compounds; esters; and alcohols. Many fragrance ingredients contain a combination of functional groups and can be categorized under two or more of the above classes.

From the standpoint of the fragrancer, it is convenient to consider the fragrance ingredients in terms of the type of aroma it imparts rather than the particular chemical class or classes it may fall within. The fragrance components herein can be formulated to provide a variety of odor categories: a non-exclusive list includes woody, sweet, citrus, floral, fruity, animal, spice, green, musk, balsamic, chemical, and mint. A variety of exemplary fragrance ingredients are described below for several of the commonly used odor categories, long with their representative (but not necessarily exclusive) chemical categories.

Surfactants

The compositions of the present invention typically contain from about 0.01% to about 15% by weight of surfactants. The level surfactant used in the present invention depends on several variables such as, but not limited to, the alcohol/water balance, the type and level hydrophobic components in the mixture, the other ingredients in the composition, the surfactant chosen, and the stability requirements of the system. The level of surfactant should be minimized since surfactants typically provide some negative cosmetic attributes. Levels as high as about 15% can be used based on the particular application; however, more typical levels of surfactant are from about 0.01% to 5.0%. For the present invention a particularly preferred level of surfactant is from about 0.01% to about 0.5%. The particular surfactants selected for use herein depends in part on the particular characteristics of the hydrophobic components, such as the fragrance and its interaction with the surfactant. Said interactions are predictable by one skilled in the art based on the hydrophilic-lipophilic balance of said surfactant which is expressed as tile surfactants HLB value. Whether the surfactant is useful in the present invention is determined experimentally by comparing the particular fragrance's solubility in a mixture of known HLB available in references such as the CTFA. This technique is widely known in the art and is fully described in *The HLB System*, ICI Americas Incorporated, May 1992.

Nonionic surfactants are particularly preferred in the present invention as they efficiently solubilize hydrophobic components in the lotion, such as fragrances, thereby maintaining clarity of said lotion. Suitable nonionic surfactants include 1) polyalkylene glycol ethers of fatty alcohols, 2) polyethylene oxide condensates of alkyl phenols, 3) condensation products of ethylene oxide with the reaction product of propylene oxide and ethylene diamine, 4) alcohol ethoxylates, 5) polysorbates, 6) polyethylene glycol (PEG) glyceryl fatty esters, 7) polyalkylene oxide modified dimethylpolysiloxanes, and mixtures thereof.

1) Polyalkylene glycol ethers of fatty alcohols are the condensation products of $C_8$ to $C_{18}$ fatty alcohols (straight or branched chain) or fatty oils (such as castor oil or lanolin oil) with ethylene glycol, polyoxyethylene, polyoxypropylene or mixtures thereof having molar ratios of from about 2–200 moles of ethylene glycol, polyoxyethylene, polyoxypropylene or mixtures thereof per mole of fatty aclohol or fatty oil. Such materials include, for example, Synperionic series of surfactants, available from ICI Surfactants of Wilmington, Del., USA and the Eumulgin HRE series available from Henkle Corporation—Emery Group, Cincinnati, Ohio, USA.

2) Polyethylene oxide condensates of alkyl phenols are the condensation products of $C_6$ to $C_{20}$ alkyl phenols with ethylene oxide having molar ratios of from about 10–60 moles of ethylene oxide per mole of alkyl phenol.

3) The condensation products of ethylene oxide with the reaction product of propylene oxide and ethylene diamine include surfactants with about 40%–80% polyoxyethylene by weight having a molecular weight of from about 5,000–11,000, wherein the ethylene diamine/propylene oxide portion has a molecular weight of about 2,500–3,000;

4) Alcohol ethoxylates are the condensation products of $C_8$ to $C_{18}$ aliphatic alcohols (straight or branched chain) with ethylene oxide have from about 10 to 60 moles of ethylene oxide per mole of alcohol.

5) Polysorbates include sucrose esters of fatty acids with mixtures fatty acid ester of sorbitol and sorbitol anhydrides condensed with approximately 4 to approximately 25 moles of ethylene oxide (such compounds are sold under the TWEEN trademane from ICI Surfactants).

6) Polyethylene glycol (PEG) glyceryl fatty esters, as depicted by the formula $RC(O)OCH_2CH(OH)CH_2(OCH_2CH_2)_nOH$ wherein n is from about 5 to about 200 and RC(O)— is an ester wherein R comprises an aliphatic radical having from about 7 to 19 carbon atoms.

7) Polyalkylene oxide modified dimethylpolysiloxanes, also known as dimethicone copolyols. These materials include the polyalkylene oxide modified dimethylpolysiloxanes of the following formula:

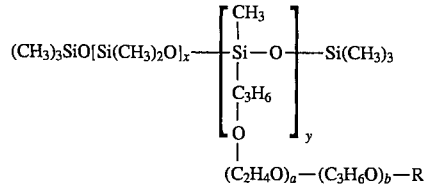

wherein R is hydrogen, an alkyl group having from 1 to about 12 carbon atoms, an alkoxy group having from 1 to about 6 carbon atoms or a hydroxyl group R' and R'' are alkyl groups having from 1 to about 12 carbon atoms; x is an integer of from 1 to 100, preferably from 20 to 30; y is an integer of 1 to 20, preferably from 2 to 10; and a and b are integers of from 0 to 50, preferably from 20 to 30. Preferred dimethicone copolyols are those of the formula:

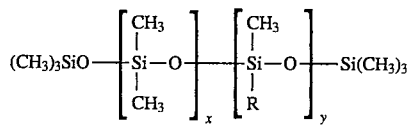

wherein X is from about 1 to about 100, y is from about 1 to about 20, and R is random EO/PO or just PO or just EO and can also contain carbon chains as in $C_{20}$–$C_{22}$ triglycerides, stearyl, or cetyl.

Dimethicone copolyols are disclosed in the following patent documents, all incorporated herein by reference herein: U.S. Pat. No. 4,122,029,Geen et al, issued Oct. 24, 1978; U.S. Pat. No. 4,265,878, issued May 5, 1981; and U.S. Pat. No. 4,421,769, Dixon et al., issued Dec. 20, 1983. Commercially available dimethicone copolyols, useful herein, include Silwet Surface Active Copolymers (manufactured by the Union Carbide Corporation); Dow Corning Silicone Surfactants (manufactured by Dow Corning Corporation); Silicone Copolymer F-754 (manufactured by SWS Silicones Corp.) Rhodorsil 70646 Fluid (manufactured by Rhone Poulenc, Inc.); and Fancorsil LIM-1 (dimethicone copolyol eicosinate) from The Fanning Corp. (Chicago, Ill., USA).

Preferred surfactants include polysorbates, alcohol ethoxylates, polyalkylene glycol ethers of fatty alcohols, and mixtures thereof.

EXAMPLES

Given below are examples of after shave lotions of the present invention.

| Ingredient(wt. %) | Examples 1–6 | | | | | |
|---|---|---|---|---|---|---|
| | 1 | 2 | 3 | 4 | 5 | 6 |
| Alcohol | 50.00 | 55.00 | 45.00 | 55.00 | 55.00 | 50.00 |
| Water | 41.50 | 38.15 | 46.80 | 37.30 | 34.60 | 42.05 |
| Perfume Component | 3.00 | 1.00 | 1.50 | 3.00 | 4.00 | 3.00 |
| Surfactant[1] | 0.20 | 0.10 | 0.20 | 0.20 | 0.15 | 0.20 |
| Anti-Inflammatory[2] | 4.00 | 2.00 | 2.00 | 2.00 | 1.00 | 2.00 |
| Moisturizing Emollient[3] | 0.80 | 3.00 | 4.00 | 2.00 | 5.00 | 2.00 |
| Skin Conditioning Agent[4] | 0.50 | 0.75 | 0.50 | 0.50 | 0.25 | 0.75 |

| Ingredient(wt. %) | Examples 7–10 | | | |
|---|---|---|---|---|
| | 7 | 8 | 9 | 10 |
| Alcohol | 50.00 | 55.00 | 45.00 | 55.00 |
| Water | 41.80 | 37.15 | 47.80 | 36.80 |
| Perfume Component | 3.00 | 1.00 | 1.50 | 3.00 |
| Surfactant[1] | 0.20 | 0.10 | 0.20 | 0.20 |
| Anti-Inflammatory[2] | 1.50 | 3.00 | 3.00 | 3.00 |
| Moisturizing Emollient[3] | 3.00 | 3.00 | 2.00 | 1.50 |
| Skin Conditioning Agent[4] | 0.50 | 0.75 | 0.50 | 0.50 |

[1]Polyethylene Glycol(40) Castor Oil, Hydrogenated (available as Cremophor RH 40), BASF Wyandotte Corporation
[2]D(+)-Pantothenyl Alcohol, Hoffamann-La Roche Incorporated
[3]Sodium Isostearoyl Lactylate
[4]Hydrolyzed Silk The composition is made by combining the components in a suitable vessel equipped with a mixer. For the present examples, the addition order is not critical; but, may control the rate of solubilization. Based on choice of 1–4, heat or addition order may be used to reduce solubilization time. If heat is used, the Perfume Component is typically added last to prevent shift in odor character due to volatilization of the higher volatile fragrance components, if present. Care must be taken when applying heat an ethanolic product. The examples provide a quick drying fragranced product that imparts moisturization and a smooth skin feel in addition to the reduction in sting and burn.

What is claimed is:

1. A low stinging and burning moisturizing after shave lotion consisting essentially of:

a. from about 20% to about 80% of a C1 to C6 monohydric alcohol;

b. from about 1.5% to about 5.0% of an anti-inflammatory agent; selected from derivatives of pantothenic acid, pantothenic ether, and mixtures thereof; and c. from about 0.5% to about 5.0% of a moisturizing emollient wherein the moisturizing emollient is an acyl lactylate having the formula:

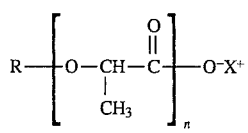

wherein R is a branched, straight, or a combination of a branched and a straight chained alkoyl group having from about 6 to about 30 carbons, X is an alkali metal ion, and n is from about 1 to about 4; wherein the ration of b:c is from about 1:5 to about 5:1.

2. The lotion of claim 1 wherein the C1 to C6 monohydric alcohol is selected from the group consisting of methanol, ethanol, isopropanol, propanol and mixtures thereof.

3. The lotion of claim 1 wherein the acyl lactylate has a R group selected from the group consisting of caproyl, myristoyl, stearoyl, lauroyl, and mixtures thereof, and said metal ion X is selected from the group consisting of sodium, potassium and mixtures thereof.

4. The lotion of claim 3 wherein the acyl lactylate has a R group comprising a branched $C_{17}H_{35}CO$ isostearoyl group, X is sodium, and n is from about 1 to 3.

5. The lotion of claim 1 wherein the anti-inflamatory agent is selected from the group consisting of d-panthenol, I-panthenol and mixtures thereof.

6. The lotion of claim 4 wherein the anti-inflammatory agent is d-panthenol.

7. The lotion of claim 6 wherein the ratio of the anti-inflammatory agent and the moisturizing emollient is from about 2:7 to about 7:2.

8. A lotion according to claim 1 additionally comprising:
   a. from about 0.2% to about 0.75% of a skin conditioning agent
   b. from about 10% to about 80% of a polar co-solvent; and
   c. from about 0.1% to about 5.0% fragrance; and
   d. from 0.01% to about 0.50% of a surfactant.

9. The lotion of claim 8 wherein the skin conditioning agent elected from the group consisting of silks, powders, silicones, and mixtures thereof.

10. The lotion of claim 8 wherein the polar co-solvent is selected from the group consisting of propylene glycol, dipropylene glycol, water, and mixtures thereof.

11. The lotion of claim 8 wherein the surfactant is selected from the group consisting of polyethylene glycol derrivatives of castor oil, polyethylene glycol ether of tridecyl alcohol, propoxylated/ethoxylated fatty alcohols, and mixtures thereof.

12. A lotion according to claim 8 additionally comprising a skin coolant from about 0.01% to about 0.25% elected from the group consisting of N,2, 3,-trimethyl-2-isopropylbutanamide, N-ethyl p-methan-3-carboxamide, and mixtures thereof.

13. A low-stinging, low-burning after shave lotion comprising:
   a. from about 50% to about 70% ethanol;
   b. from about 1.5% to about 3.0% d-panthenol; and
   c. from about 1.5% to about 3.0% sodium isostearoyl-2-lactylate; wherein the ratio of c:b is from 1:2 to 2:1.

14. An after shave lotion of claim 13 additionally comprising:
   a. from about 0.30% to about 0.50% of a solution of fibroin silk;
   b. from about 30% to about 50% water;
   c. from about 2% to about 4% fragrance; and
   d. from about 0.01% to about 0.05% polyethylene glycol ethers of tridecyl alcohol.

* * * * *

UNITED STATES PATENT AND TRADEMARK OFFICE
CERTIFICATE OF CORRECTION

PATENT NO. : 5,527,530
DATED : June 18, 1996
INVENTOR(S) : M. S. Simmons, L. S. Lisboa, E. A. Ferguson It is certified that error appears in the above-indentified patent and that said Letters Patent is hereby corrected as shown below:

Column 4, line 10 "latcylate" should read --lactylate--.

Column 9, line 25, claim 5, "I-panthenol" should read --l-panthenol--.

Signed and Sealed this

Eighteenth Day of February, 1997

Attest:

BRUCE LEHMAN

*Attesting Officer*  *Commissioner of Patents and Trademarks*